United States Patent
Werbach et al.

(10) Patent No.: US 10,018,491 B2
(45) Date of Patent: Jul. 10, 2018

(54) VIBRATING SENSOR ASSEMBLY WITH A ONE-PIECE CONDUIT MOUNT

(71) Applicant: Micro Motion, Inc., Boulder, CO (US)

(72) Inventors: Christopher A Werbach, Longmont, CO (US); Gregory Treat Lanham, Longmont, CO (US); Bethany Pickett, Golden, CO (US)

(73) Assignee: Micro Motion, Inc., Boulder, CO (US)

( * ) Notice: Subject to any disclaimer, the term of this patent is extended or adjusted under 35 U.S.C. 154(b) by 462 days.

(21) Appl. No.: 14/423,386

(22) PCT Filed: Sep. 18, 2012

(86) PCT No.: PCT/US2012/055912
§ 371 (c)(1),
(2) Date: Feb. 23, 2015

(87) PCT Pub. No.: WO2014/046643
PCT Pub. Date: Mar. 27, 2014

(65) Prior Publication Data
US 2015/0260559 A1    Sep. 17, 2015

(51) Int. Cl.
*G01N 1/20*    (2006.01)
*G01F 1/66*    (2006.01)
(Continued)

(52) U.S. Cl.
CPC ............ *G01F 1/662* (2013.01); *G01F 1/667* (2013.01); *G01F 1/8404* (2013.01); *G01F 1/8409* (2013.01); *G01F 1/8413* (2013.01); *G01F 1/8486* (2013.01); *G01F 15/14* (2013.01); *G01F 15/18* (2013.01); *G01H 1/00* (2013.01); *G01N 1/20* (2013.01); *G01N 1/2035* (2013.01);
(Continued)

(58) Field of Classification Search
CPC ...... G01N 1/20; G01N 1/2035; G01N 1/2064; G01N 1/18; G01N 1/2202; G01F 1/662; G01F 1/667; G01F 1/8409; G01F 1/8413; G01F 15/14; G01F 15/18; G01F 15/185; G01H 1/00; Y10T 29/494
USPC .................... 73/863.41, 863.44, 863.61, 649
See application file for complete search history.

(56) References Cited

U.S. PATENT DOCUMENTS 4,730,501 A * 3/1988 Levien ................. G01F 1/8413
73/861.357
4,747,312 A 5/1988 Herzel
(Continued)

FOREIGN PATENT DOCUMENTS

CN    101903753 A    12/2010
CN    102460083 A    5/2012
(Continued)

*Primary Examiner* — Manish S Shah
*Assistant Examiner* — Rose M Miller
(74) *Attorney, Agent, or Firm* — The Ollila Law Group LLC (57) ABSTRACT

A vibrating sensor assembly (200) is provided. The vibrating sensor assembly (200) includes a one-piece conduit mount (205). The one-piece conduit mount (205) includes an inlet port (206), an outlet port (208), and a conduit support base (210) extending from the inlet port (206) to the outlet port (208). The vibrating sensor assembly (200) further includes a single fluid conduit (203) with two or more loops (204A, 204B) separated by a crossover section (213), which is coupled to the one-piece conduit mount (205).

13 Claims, 5 Drawing Sheets

(51) Int. Cl.
  *G01F 1/84* (2006.01)
  *G01F 15/14* (2006.01)
  *G01F 15/18* (2006.01)
  *G01H 1/00* (2006.01)
  *G01N 1/22* (2006.01)
  *G01N 1/18* (2006.01)

(52) U.S. Cl.
  CPC .............. *G01N 1/18* (2013.01); *G01N 1/2202* (2013.01); *Y10T 29/494* (2015.01)

(56) References Cited

U.S. PATENT DOCUMENTS

| | | | |
|---|---|---|---|
| 4,825,705 A * | 5/1989 | Hohloch | G01F 1/8404 73/861.355 |
| 4,891,991 A * | 1/1990 | Mattar | G01F 1/8413 73/861.355 |
| 5,355,737 A | 10/1994 | Lew et al. | |
| 5,425,277 A | 6/1995 | Lew | |
| 5,663,509 A | 9/1997 | Lew et al. | |
| 5,996,225 A * | 12/1999 | Ollila | G01F 1/8404 29/888.09 |
| 6,293,158 B1 | 9/2001 | Ollila et al. | |
| 8,359,933 B2 | 1/2013 | Drahm et al. | |
| 8,671,779 B2 | 3/2014 | Van Cleve | |
| 2003/0097882 A1 | 5/2003 | Schlosser et al. | |
| 2006/0243067 A1* | 11/2006 | Mehendale | G01F 1/8409 73/861.355 |

FOREIGN PATENT DOCUMENTS

| | | |
|---|---|---|
| CN | 102460084 A | 5/2012 |
| CN | 102667420 A | 9/2012 |
| EP | 0246510 A1 | 11/1987 |
| JP | 64-086219 A | 3/1989 |
| WO | 2009078880 A1 | 6/2009 |
| WO | 2010144083 A1 | 12/2010 |

* cited by examiner

VIBRATING SENSOR ASSEMBLY WITH A ONE-PIECE CONDUIT MOUNT

TECHNICAL FIELD

The embodiments described below relate to, vibrating sensor assemblies, and more particularly, to a vibrating sensor assembly mounted on a one-piece conduit mount.

BACKGROUND OF THE INVENTION

Vibrating fluid sensors, such as Coriolis mass flow meters and vibrating densitometers typically operate by detecting motion of a vibrating conduit that contains a flowing material. Properties associated with the fluid in the conduit, such as mass flow, density and the like, can be determined by processing measurement signals received from motion transducers associated with the conduit. The vibration modes of the vibrating material-filled system generally are affected by the combined mass, stiffness, and damping characteristics of the containing conduit and the material contained therein.

A typical vibrating fluid meter includes one or more fluid conduits that are connected inline in a pipeline or other transport system and convey material, e.g., fluids, slurries and the like, in the system. Each conduit may be viewed as having a set of natural vibration modes, including for example, simple bending, torsional, radial, and coupled modes. In a typical Coriolis mass flow measurement application, a conduit is excited in one or more vibration modes as a material flows through the conduit, and motion of the conduit is measured at points spaced along the conduit. Excitation is typically provided by an actuator, e.g., an electromechanical device, such as a voice coil-type driver, that perturbs the conduit in a periodic fashion. Mass flow rate may be determined by measuring time delay or phase differences between motions at the transducer locations. Two such transducers (or pick-off sensors) are typically employed in order to measure a vibrational response of the flow conduit or conduits, and are typically located at positions upstream and downstream of the actuator. The two pickoff sensors are connected to electronic instrumentation by cabling, such as by two independent pairs of wires. The instrumentation receives signals from the two pickoff sensors and processes the signals in order to derive a mass flow rate measurement.

One type of vibrating meter uses a single loop, serial path flow conduit to measure mass flow. However, the use of a single loop, serial path flow conduit design has an inherent disadvantage in that it is unbalanced and may be affected by external vibrations to a greater extent than other types of meters. A single loop, serial flow Coriolis flow meter has a single curved conduit or loop extending in cantilever fashion from a solid mount. The flow meter must include a rigid structure positioned next to the flow conduit against which the flow conduit can vibrate. The use of the rigid structure can be impractical in many industrial applications.

Another prior art approach uses a dual loop, parallel flow conduit configuration. Dual loop, parallel flow conduit flow meters are balanced and changes in density affect both of the parallel flow conduits substantially evenly. The parallel flow conduits are driven to oscillate in opposition to one another with the vibrating force of one flow conduit canceling out the vibrating forces of the other flow conduit. Therefore, in many applications, a dual loop parallel flow conduit configuration is desirable. However, because the flow is split between two parallel flow conduits, each of the flow conduits is smaller than the connected pipeline. This can be problematic for low flow applications. Specifically, the smaller flow conduits required in dual loop, parallel flow conduit flow meters are more prone to plugging and the manifold used to split the flow between the flow conduits results in a higher pressure drop.

The above mentioned problems can be solved by using a dual loop, serial flow path flow meter. The dual loop, serial flow path flow meter combines the advantages of the single loop flow meter and the dual loop, parallel path flow meter.

Figure 1:
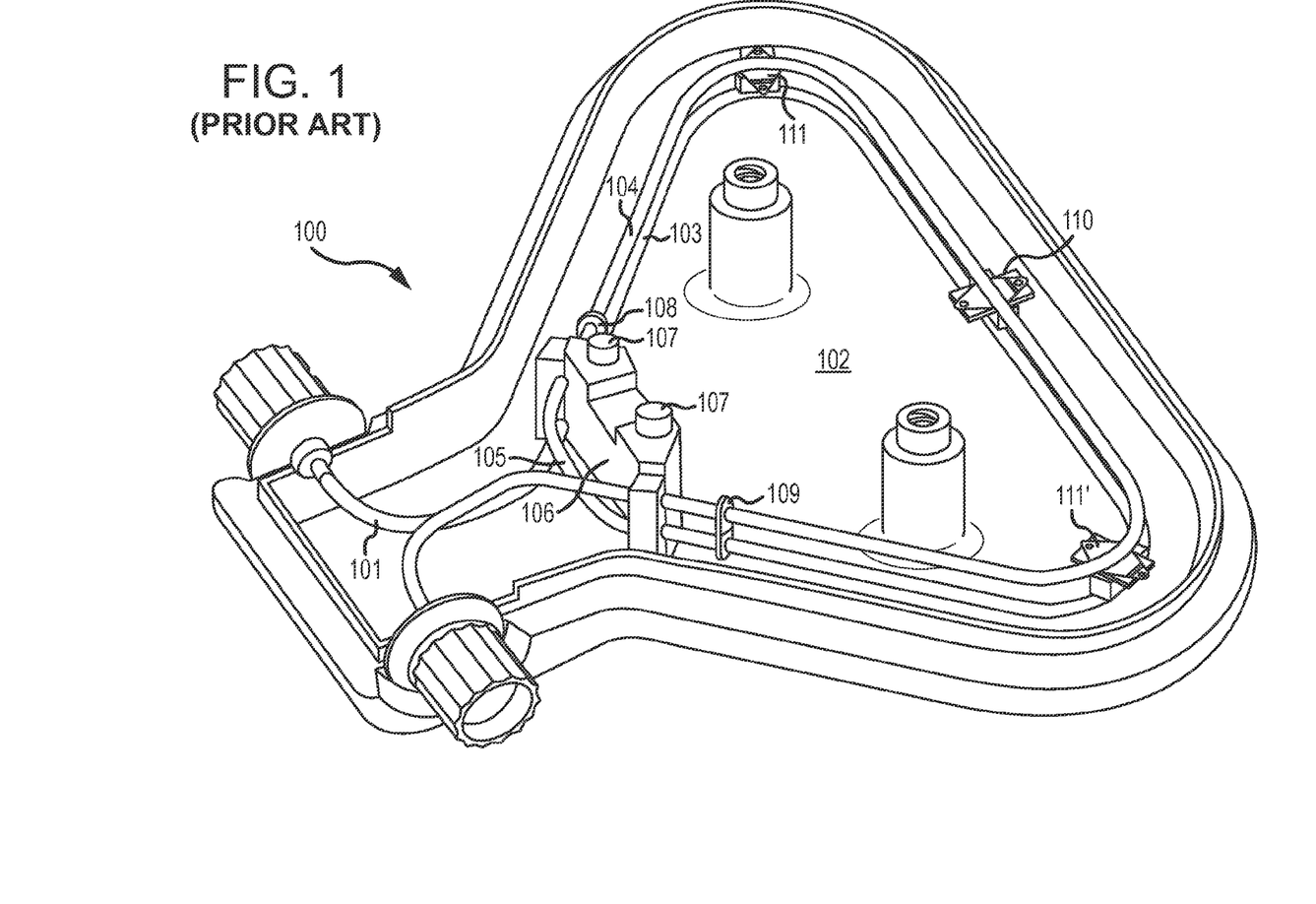
FIG. 1 shows a prior art dual loop, serial flow path flow meter.

FIG. 1 shows a portion of a prior art dual loop, serial flow path flow meter 100. The flow meter 100 is shown and described in more detail in U.S. Pat. No. 6,332,367, assigned on its face to the present applicants, and incorporated herein by reference for all that it teaches. The flow meter 100 includes a single flow conduit 101, which is contained within a housing 102. The flow conduit 101 includes two loops 103, 104, which lie in planes that are parallel to one another. The loops 103, 104 vibrate in response to a signal applied by the driver 110. Pick-offs 111, 111' can detect the motion of the loops 103, 104 to determine various fluid characteristics. The loops 103, 104 are joined together with a crossover section 105. The crossover section 105 joins the two loops to form the continuous flow conduit 101. The crossover section 105 along with the two loops 103, 104 are connected and secured using an anchor 106. Although the anchor 106 is coupled to the housing 102 using pins 107, external vibrations are still experienced by the vibrating portion of the flow conduit 101 (above the brace bars 108, 109). Further, as shown, the crossover section 105 simply hangs freely and is not supported in any manner. As the length of the crossover section 105 increases, the lack of support can become problematic and result in erroneous measurements as the crossover section 105 can be subjected to distortions.

Therefore, while the prior art dual loop, serial flow path flow meter 100 provides an adequate flow meter in some situations, there is still a need to further limit external vibrations experienced by the pick-offs as well as provide a better support for the crossover section. The embodiments described below overcome these and other problems and an advance in the art is provided. The embodiments described below provide a dual loop, serial flow path flow meter mounted on a one-piece conduit support. The one-piece conduit support can adequately support the conduit's crossover section while minimizing external vibrations experienced by the flow conduit's pick-offs. Therefore, more accurate flow rates can be determined in more diverse environments.

SUMMARY OF THE INVENTION

A one-piece conduit mount for a vibrating sensor assembly is provided according to an embodiment. The one-piece conduit mount comprises an inlet port and an outlet port. According to an embodiment, the one-piece conduit mount further comprises a conduit support base extending from the inlet port to the outlet port. According to an embodiment, the one-piece conduit mount further comprises first and second support blocks extending from the conduit support base.

A vibrating sensor assembly is provided according to an embodiment. The vibrating sensor assembly comprises a one-piece conduit mount including an inlet port, an outlet port, and a conduit support base extending from the inlet port to the outlet port. According to an embodiment, the vibrating sensor assembly further comprises a single fluid conduit with two or more loops separated by a crossover section, which is coupled to the one-piece conduit mount.

A method for forming a vibrating sensor assembly is provided according to an embodiment. The method comprises a step of forming a single fluid conduit into two or more loops. The method further comprises a step of separating the two or more loops with a crossover section. According to an embodiment, the method further comprises a step of coupling a one-piece conduit mount to the crossover section, wherein the one-piece conduit mount includes an inlet port, an outlet port, and a conduit support base extending from the inlet port to the outlet port.

ASPECTS

According to an aspect, a one-piece conduit mount for a vibrating sensor assembly comprises:
an inlet port;
an outlet port;
a conduit support base extending from the inlet port to the outlet port; and
first and second support blocks extending from the conduit support base.

Preferably, the first and second support blocks are tapered and comprise a first thickness, $t_1$ on an end facing a corresponding port and comprise a second thickness, $t_2$ on an end facing the other support block, wherein $t_2$ is less than $t_1$.

Preferably, the one-piece conduit mount further comprises one or more apertures sized and shaped to receive a coupling fixture.

According to another aspect, a vibrating sensor assembly comprises:
a one-piece conduit mount including an inlet port, an outlet port, and a conduit support base extending from the inlet port to the outlet port; and
a single fluid conduit with two or more loops separated by a crossover section, which is coupled to the one-piece conduit mount.

Preferably, the crossover section is coupled to the conduit support base.

Preferably, the vibrating sensor assembly further comprises first and second support blocks extending from the conduit support base.

Preferably, a first loop of the two or more loops is coupled to a first side of the first and second support blocks and wherein a second loop of the two or more loops is coupled to a second side of the first and second support blocks.

Preferably, the vibrating sensor assembly further comprises an inlet conduit portion coupled to the inlet port.

Preferably, the vibrating sensor assembly further comprises an outlet conduit portion coupled to the outlet port.

Preferably, the vibrating sensor assembly further comprises a case at least partially enclosing the fluid conduit.

According to another aspect, a method for forming a vibrating sensor assembly comprises steps of:
forming a single fluid conduit into two or more loops;
separating the two or more loops with a crossover section; and
coupling a one-piece conduit mount to the crossover section, wherein the one-piece conduit mount includes an inlet port, an outlet port, and a conduit support base extending from the inlet port to the outlet port.

Preferably, the step of coupling comprises coupling the crossover section to the conduit support base.

Preferably, the one-piece conduit mount comprises first and second support blocks and the step of coupling comprises:
coupling a first loop of the two or more loops to a first side of the first and second support blocks; and
coupling a second loop of the two or more loops to a second side of the first and second support blocks.

Preferably, the step of coupling comprises coupling an inlet conduit portion to an inlet port of the one-piece conduit mount and coupling an outlet conduit portion to an outlet port of the one-piece conduit mount.

Preferably, the method further comprises a step of at least partially enclosing the fluid conduit with a case.

DETAILED DESCRIPTION OF THE INVENTION

FIGS. 2-5 and the following description depict specific examples to teach those skilled in the art how to make and use the best mode of embodiments of a vibrating meter. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the vibrating meter. As a result, the embodiments described below are not limited to the specific examples described below, but only by the claims and their equivalents.

Figure 2:
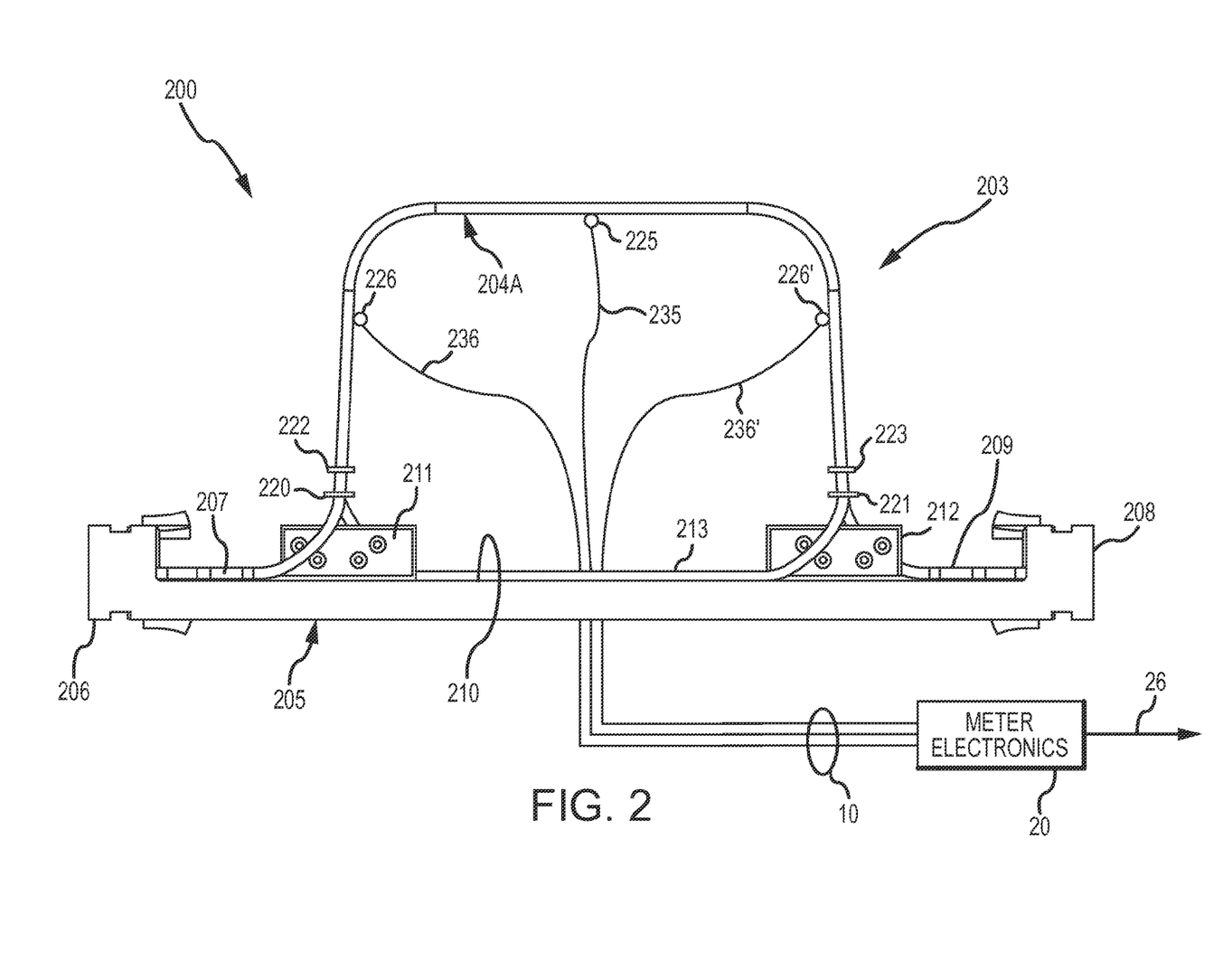
FIG. 2 shows a vibrating meter according to an embodiment.

FIG. 2 shows a vibrating meter 5 according to an embodiment. The vibrating meter 5 comprises a sensor assembly 200 and a meter electronics 20. The sensor assembly 200 and the meter electronics 20 can be in electrical communication with one another via leads 10. The vibrating meter 5 is shown as comprising a Coriolis flow meter. However, those skilled in the art will readily recognize that the vibrating meter 5 may comprise other types of sensors that lack the measurement capabilities of Coriolis flow meters. For example, the vibrating meter 5 may comprise a vibrating densitometer, a vibrating volumetric flow meter, etc. Therefore, while the discussion that follows relates to a Coriolis flow meter, the embodiments should in no way be so limited.

According to an embodiment, the sensor assembly 200 comprises a single fluid conduit 203, which forms two or more loops 204A, 204B to create a dual loop, serial flow path sensor assembly. Therefore, while two loops 204A, 204B are shown in the figures and described, the sensor assembly 200 may include more than two loops while remaining within the scope of the claims that follow. According to an embodiment, the fluid conduit 203 is mounted on a one-piece conduit mount 205. As can be appreciated, the fluid conduit 203 and the one-piece conduit mount 205 can be enclosed by a case (See FIG. 5) during use. The one-piece conduit mount 205 can be coupled to the fluid conduit 203 at more than one location. For example, the one piece conduit mount 205 can comprise an inlet port 206, which can be coupled to a fluid pipeline (not shown). An inlet conduit portion 207 of the fluid conduit 203 can be received by the inlet port 206. The one-piece conduit mount 205 can also comprise an outlet port 208, which can be coupled to the fluid pipeline and also receive an outlet conduit portion 209. According to an embodiment, the inlet and outlet conduit portions 207, 209 can be coupled to the inlet and outlet ports 206, 208 to form fluid-tight connections. Additionally, a portion of the inlet and outlet conduit portions 207, 209 can be coupled to a conduit support base 210 (See FIG. 4, for example) of the one-piece conduit mount 205. According to an embodiment, the conduit support base 210 can extend substantially completely between the inlet and outlet ports 206, 208. The conduit support base 210 can provide a suitable mounting surface for various portions of the fluid conduit 203.

According to an embodiment, the fluid conduit 203 can extend from the inlet conduit portion 207 towards the first loop 204A. According to the embodiment shown, as the fluid conduit 203 extends upwards away from the conduit support base 210 to form the first loop 204A, the fluid conduit 203 can be coupled to a first support block 211. The first support block 211 can be coupled to the conduit support base 210 or may comprise an integral portion of the conduit support base 210, for example. The first support block 211 is shown extending from the conduit support base 210 upwards as shown in the figures.

The fluid conduit 203 can extend away from the first support block 211 where it forms the first loop 204A. The first loop 204A can also be coupled to a second support block 212. The first and second support blocks 212 can help support the first and second loops 204A, 204B and aid in defining the loops' bending axes (See FIG. 5). The first and second support blocks 211, 212 can also help position the first and second loops' planes, P1, P2 (See FIG. 3). According to an embodiment, the fluid conduit 203 is coupled to the second support block 212 as the conduit 203 exits the first loop 204A and enters the crossover section 213. According to an embodiment, the crossover section 213 provides the transition between the first and second loops 204A, 204B.

According to an embodiment, the crossover section 213 can be coupled to the one-piece conduit mount 205. More specifically, in the embodiment shown, the crossover section 213 can be coupled to the conduit support base 210. The crossover section 213 can be coupled to the conduit support base 210 using a variety of methods such as brazing, welding, mechanical fasteners, adhesives, etc. The particular method used for coupling the crossover section 213 to the conduit support base 210 is not important for purposes of the present application and should in no way limit the claims that follow. According to an embodiment, the crossover section 213 may be coupled to the conduit support base 210 in multiple locations. As can be appreciated, unlike the anchor 106 of the prior art vibrating meter 100, which allows the crossover section 105 to hang freely, the one-piece conduit mount 205 is coupled to the crossover section 213 to ensure that the crossover section 213 is properly supported. As shown, the crossover section 213 is coupled to a top surface (during normal orientation) of the one-piece conduit mount 205 such that the weight of the crossover section 213 can be supported by the conduit support base 210. Therefore, vibrations and stresses that are experienced by the crossover section 213 can be minimized. Furthermore, because the conduit support 213 is formed of one piece, stresses that may be experienced as the case 500 is installed or when the sensor assembly 200 is installed in the pipeline can be absorbed by the conduit mount 205 rather than the fluid conduit 203.

As the fluid conduit 203 extends from the crossover section 213 towards the second loop 204B, the fluid conduit 203 can be coupled to the first support block 211 once again. However, as the fluid conduit 203 enters the second loop 204B, the fluid conduit 203 is coupled to the opposite side of the first support block 211. The fluid conduit 203 creates the second loop 204B and extends towards the outlet conduit portion 209. According to an embodiment, the fluid conduit 203 can also be coupled to the second support block 212 as the fluid conduit 203 transitions from the second loop 204B to the outlet conduit portion 209.

With the fluid conduit 203 securely coupled to the one-piece conduit mount 205, a driver 225 can vibrate the first and second loops 204A, 204B in phase opposition about bending axes W-W, W'-W' (See FIG. 5), which are at least partially defined by brace bars 220-223. The driver 225 can receive a drive signal via lead 235 from the meter electronics 20. As the first and second loops 204A, 204B vibrate, the motion can be detected by first and second pick-off sensors 226, 226'. The pick-off signals can be transmitted to the meter electronics 20 via leads 236, 236' to determine one or more fluid characteristics of the fluid within the fluid conduit 203, such as a mass flow rate, a volume flow rate, a density, a temperature, etc.

Figure 3:
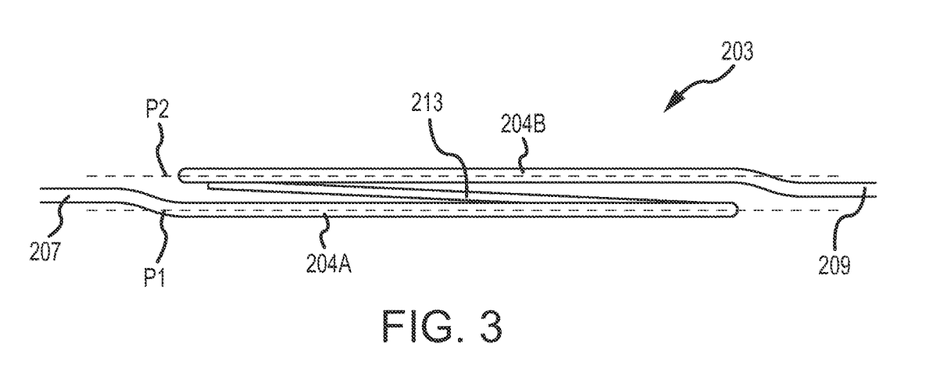
FIG. 3 shows a top view of the fluid conduit according to an embodiment.

FIG. 3 shows a top view of the fluid conduit 203 according to an embodiment. In FIG. 3, the fluid conduit 203 is shown prior to being coupled to the one-piece conduit mount 205. As can be seen, the fluid conduit 203 includes the inlet conduit portion 207, which transitions into the first loop 204A. Near the end of the first loop 204A, the fluid conduit 203 transitions into the crossover section 213. According to an embodiment, the crossover section 213 can join the first and second loops 204A, 204B. The crossover section 213 traverses from the first plane P1 to the second plane P2. The second loop 204B then ends at the outlet conduit portion 209. According to an embodiment, the first and second loops 204A, 204B are in substantially parallel planes P1, P2, respectively. As discussed above, in some embodiments, the first and second support blocks 211, 212 can help define the planes P1, P2. By providing the two loops in parallel planes, the two loops 204A, 204B can be vibrated with respect to one another and can act as a dual loop, parallel flow path flow meter even though the two loops 204A, 204B comprise a serial flow path.

Figure 4:
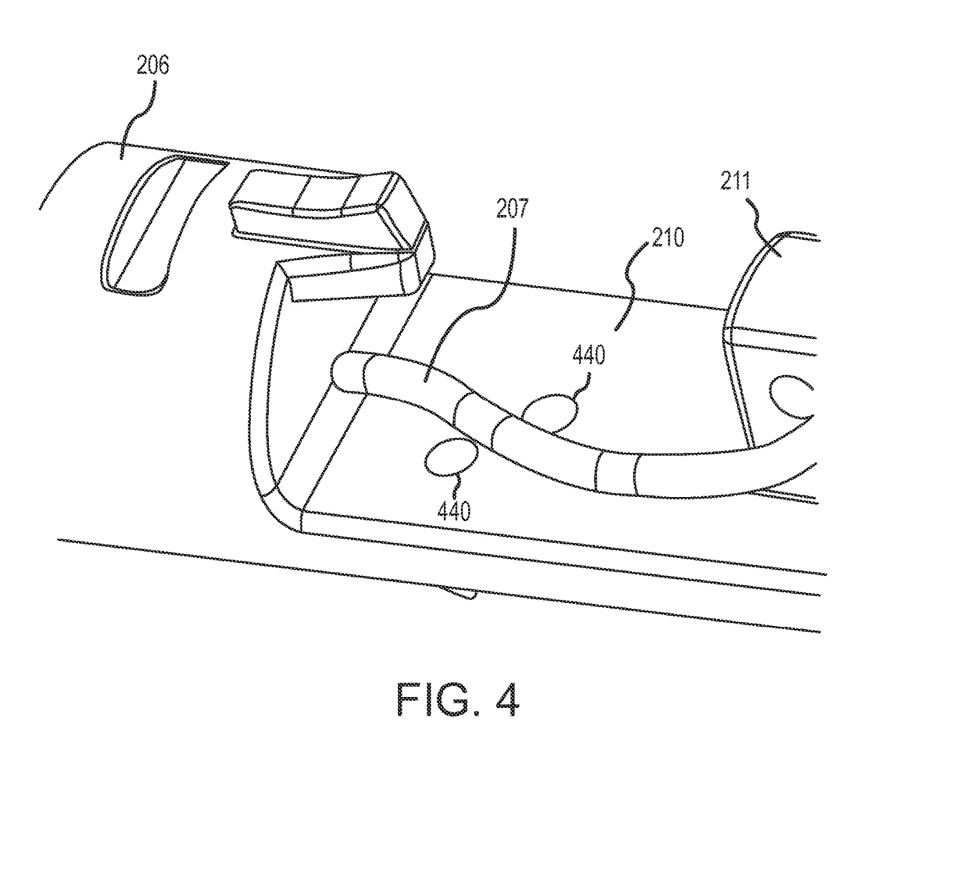
FIG. 4 shows the inlet portion of the fluid conduit coupled to the conduit support base according to an embodiment.

FIG. 4 shows a portion of the sensor assembly 200 according to an embodiment. In FIG. 4, a better view of the inlet portion 207, which is coupled to the conduit support base 210 is shown. The conduit support base 210 includes two apertures 440. The apertures 440 can be provided to receive a fixture (not shown) used in coupling the fluid conduit 203 to the one-piece conduit mount 205.

Figure 5:
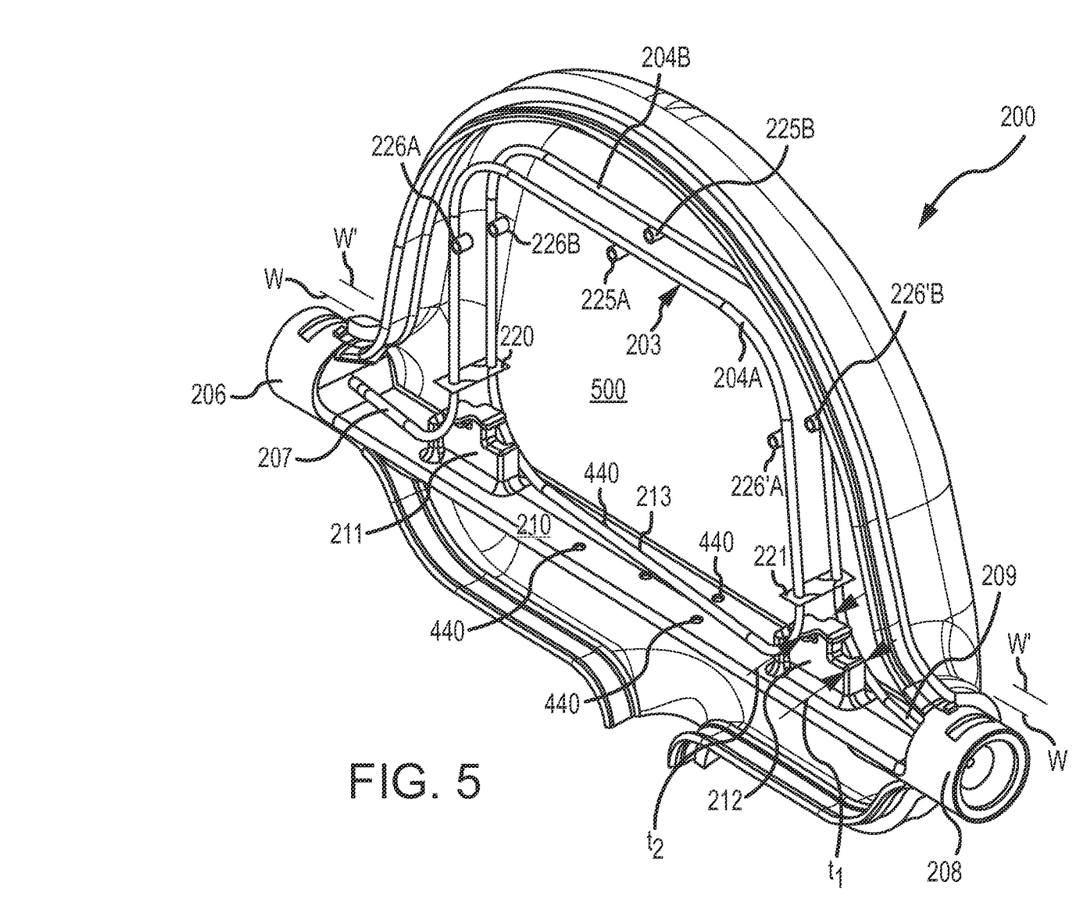
FIG. 5 shows the sensor assembly according an embodiment.

FIG. 5 shows another view of the sensor assembly 200 according to an embodiment. In FIG. 5, a portion of the case 500 is now provided. As can be appreciated, another corresponding case portion can be coupled to the portion shown to fully enclose the fluid conduit 203.

In FIG. 5, the conduit support base 210 is shown in better detail. As can be seen in FIG. 5, the crossover section 213 extends between the first and second support blocks 211, 212. A plurality of apertures 440 are shown in the one-piece conduit mount 205, which are provided to accommodate coupling fixtures used in coupling the fluid conduit 203 to the conduit mount 205.

In the embodiment shown, the support blocks 211, 212 can be tapered to accommodate the crossover's change from the first plane, P1 to the second plane, P2. For example, the second support block 212 is shown comprising a first width, $t_1$ at the end closest to the outlet port 208 and a second width, $t_2$ at the end closest to the first support block 211. In the embodiment shown, $t_2$ is less than $t_1$. According to an embodiment, the first support block 211 can also be tapered. In the embodiment shown, the support blocks 211, 212 can also help the brace bars 220, 221 define the bending axes W-W, W'-W'. As can be seen, the embodiment shown in FIG. 5 only includes a single brace bar 220, 221 on each end. Therefore, the support blocks 211, 212 can act as a second brace bar in some embodiments.

Also shown in FIG. 5 in more detail are the driver and pick-off components. According to an embodiment, the driver 225 comprises a first driver component 225A coupled to the first loop 204A and a second driver component 225B coupled to the second loop 204B. Likewise, the first and second pick-off sensors 226, 226' comprise a first pick-off sensor component 226A, 226'A coupled to the first loop 204A and a second pick-off sensor component 226B, 226'B coupled to the second loop 204B, respectively. As discussed above, the driver 225 and pick-off 226, 226' components may comprise a magnet/coil combination, which is generally known in the art or some other type of configuration that allows for vibration and the detection of motion of the loops 204A, 204B.

The embodiments described above provide an improved multiple loop, serial flow path vibrating meter. Unlike prior art meters that separate the fluid tube's support into multiple components, the embodiments described above comprise a one-piece conduit mount 205. The one-piece conduit mount 205 can provide better support for the fluid conduit's crossover section 213 than in the prior art. The additional support for the crossover section 213 can minimize distortions and external vibrations experienced by the pick-offs 226, 226'.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other vibrating meters, and not just to the embodiments described above and shown in the accompanying figures. Accordingly, the scope of the embodiments described above should be determined from the following claims.

We claim:

1. A one-piece conduit mount (205) for a vibrating sensor assembly (200), comprising:
    an inlet port (206);
    an outlet port (208);
    a conduit support base (210) extending from the inlet port (206) to the outlet port (208); and
    first and second support blocks (211, 212) extending from the conduit support base (210), wherein the first and second support blocks (211, 212) are tapered and comprise a first thickness, $t_1$ on an end facing a corresponding port and comprise a second thickness, $t_2$ on an end facing the other support block, wherein $t_2$ is less than $t_1$.

2. The one-piece conduit mount (205) of claim 1, further comprising one or more apertures (440) sized and shaped to receive a coupling fixture.

3. A vibrating sensor assembly (200), comprising:
    a one-piece conduit mount (205) including a fluid inlet port (206), a fluid outlet port (208), and a conduit support base (210) extending from the fluid inlet port (206) to the fluid outlet port (208);
    a single fluid conduit (203) with two or more loops (204A, 204B) separated by a crossover section (213), which is coupled to the one-piece conduit mount (205) such that the fluid inlet port and fluid outlet port are in fluid communication with the fluid conduit, and wherein the fluid inlet and outlet ports and fluid conduit are configured to have a fluid pass therethrough.

4. The vibrating sensor assembly (200) of claim 3, wherein the crossover section (213) is coupled to the conduit support base (210).

5. The vibrating sensor assembly (200) of claim 3, further comprising first and second support blocks (211, 212) extending from the conduit support base (210).

6. The vibrating sensor assembly (200) of claim 5, wherein a first loop (204A) of the two or more loops (204A, 204B) is coupled to a first side of the first and second support blocks (211, 212) and wherein a second loop (204B) of the two or more loops (204A, 204B) is coupled to a second side of the first and second support blocks (211, 212).

7. The vibrating sensor assembly (200) of claim 3, further comprising an inlet conduit portion (207) coupled to the inlet port (206).

8. The vibrating sensor assembly (200) of claim 3, further comprising an outlet conduit portion (209) coupled to the outlet port (208).

9. The vibrating sensor assembly (200) of claim 3, further comprising a case (500) at least partially enclosing the fluid conduit (203).

10. A method for forming a vibrating sensor assembly, comprising steps of:
    forming a single fluid conduit into two or more loops;
    separating the two or more loops with a crossover section; and
    coupling a one-piece conduit mount to the crossover section, wherein the one-piece conduit mount includes a fluid inlet port, a fluid outlet port, and a conduit support base extending from the fluid inlet port to the fluid outlet port, wherein that the fluid inlet port and fluid outlet port are in fluid communication with the fluid conduit, and wherein the fluid inlet and outlet ports and fluid conduit are configured to have a fluid pass therethrough.

11. The method of claim 10, wherein the step of coupling comprises coupling the crossover section to the conduit support base.

12. The method of claim 10, wherein the one-piece conduit mount comprises first and second support blocks and the step of coupling comprises:
    coupling a first loop of the two or more loops to a first side of the first and second support blocks; and
    coupling a second loop of the two or more loops to a second side of the first and second support blocks.

13. The method of claim 10, further comprising a step of at least partially enclosing the fluid conduit with a case.

\* \* \* \* \*